United States Patent [19]

Lia

[11] Patent Number: 4,727,859

[45] Date of Patent: Mar. 1, 1988

[54] RIGHT ANGLE DETACHABLE PRISM ASSEMBLY FOR BORESCOPE

[75] Inventor: Raymond A. Lia, Auburn, N.Y.

[73] Assignee: Welch Allyn, Inc., Skaneateles Falls, N.Y.

[21] Appl. No.: 947,428

[22] Filed: Dec. 29, 1986

[51] Int. Cl.[4] .......................... A61B 1/00; G02B 7/18
[52] U.S. Cl. ......................................... 128/6; 350/287
[58] Field of Search .................... 128/4, 6, 5; 350/287

[56] References Cited

U.S. PATENT DOCUMENTS

| | | | |
|---|---|---|---|
| 2,949,071 | 8/1960 | Foures | 350/287 X |
| 3,561,432 | 2/1971 | Yamaki et al. | 128/6 |
| 3,596,863 | 8/1971 | Kaspareck | 350/287 X |
| 4,571,028 | 2/1986 | Ziegler et al. | 350/287 |

*Primary Examiner*—William H. Grieb
*Attorney, Agent, or Firm*—Bruns and Wall

[57] ABSTRACT

A detachable prism assembly for a small-diameter borescope has a generally cylindrical housing with an open end that fits over a viewing head of the borescope, a prism, and a sliding prism holder within the housing. A spring urges the holder and prism proximally away from the distal end of the housing, and into contact with the front surface of the borescope head. The spring also urges a projection in the assembly into engagement with a corresponding recess in the periphery of the borescope viewing head. A manually actuable member on the detachable prism assembly must be moved by the user to move the projection out of engagement with the recess to permit detachment of the prism assembly from the borescope. The prism assembly can be attached only in its proper orientation, and cannot fall off the borescope head while in use.

11 Claims, 7 Drawing Figures

RIGHT ANGLE DETACHABLE PRISM ASSEMBLY FOR BORESCOPE

BACKGROUND OF THE INVENTION

This invention relates to borescopes and endoscopes, which are long flexible instruments which carry a viewing device at the end of an elongated insertion tube. Borescopes are intended for inspection of concealed machine parts and the like, for example, inspection of vanes of a turbine or jet engine without disassembly of same. Endoscopes are intended for examination of a human body cavity.

The invention is more particularly related to a viewing head which is demountably installed on the distal end of a borescope insertion tube.

For small borescopes, such as those of six mm diameter, a right angle optical assembly is often required. This should be detachable so that the borescope can be used for both forward viewing and side viewing, but the viewing assembly must not fall off while in use. The current approach to attachments for borescope or endoscope viewing heads is the use of threaded retaining rings and keyed structure for orientation of the optics. Bayonet attachment devices are sometimes used also. However, conventional devices are often difficult to install or remove, or else do not hold the attachment onto the borescope securely enough to ensure that the assembly will not fall off. These devices have also been impractical where a large (i.e., 5 mm) video imager is employed in a small diameter (i.e., 6 mm) borescope.

OBJECTS AND SUMMARY OF THE INVENTION

It is an object of this invention to provide a borescope (or endoscope) with a detachable right angle prism assembly which is an improvement over and avoids the drawbacks of the prior art.

Further objects of this invention are to provide a detachable right angle prism assembly which ensures proper orientation with the optical axis of the borescope, which locks positively onto the borescope, which can be readily employed with a six mm borescope having a five mm diameter solid state imager, and which is relatively simple in construction and operation.

It is yet another object of this invention to provide a detachable right angle prism assembly which is simple to attach and detach from the borescope, but which will not fall off the borescope when in use.

It is yet another object of this invention to provide such a detachable right angle prism assembly which is incapable of being assembled incorrectly onto the viewing head of the borescope.

According to an aspect of this invention, the right angle detachable prism assembly of this invention is well suited for small-diameter borescopes of the type that have a viewing head at the distal end of their insertion tubes. The viewing head has a protruding member that contains an optical image pick-up device whose optical axis is oriented along the axis of the viewing head and through a flat front surface thereof. The protruding member, which is generally cylindrical with a peripheral cutout, also has a radially projecting retaining structure thereon, which can be a thread, bayonet pin, or other equivalent structure.

The assembly of this invention has a right angle prism dimensioned to match the optical imager and with one flat face to be disposed against the flat front surface of the viewing head. A generally cylindrical housing contains the prism and has an open proximal end to fit over the viewing head with cooperating structure which engages the retaining structure on the viewing head. A prism holder is slidably disposed in the housing and securely holds the prism oriented so that the one flat face is positioned against the front surface of the viewing head. A proximally extending projection, which can be a tongue on the proximal end of the sliding holder, engages the cutout in the viewing head when the prism flat face is disposed against the viewing head front surface. A finger pin or other manually actuable member is actuable from outside the housing to release the projection from the cutout. Also, a compression spring or similar resilient member yieldably urges the prism holder proximally relative to the housing to bias the prism against the front surface of the viewing head.

The above and many other objects, features and advantages of this invention will be more fully understood from the ensuing description of a preferred embodiment, which should be considered in connection with the accompanying drawing.

DETAILED DESCRIPTION OF THE PREFERRED EMBODIMENT

Figure 1:
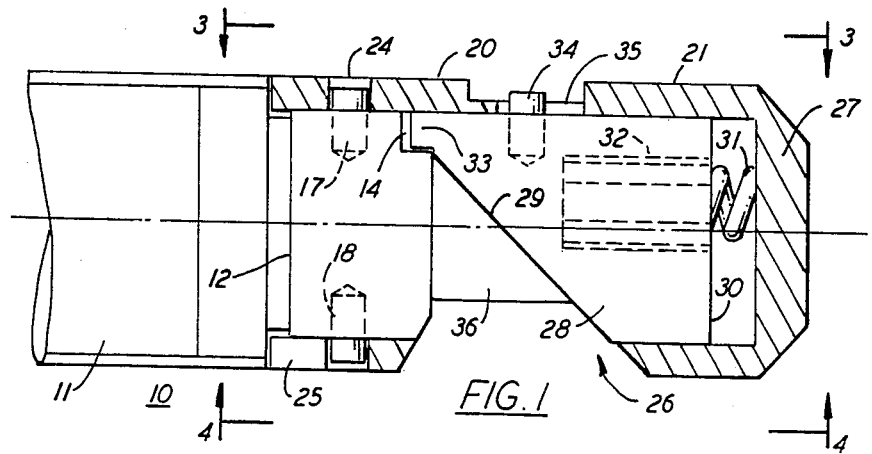
FIG. 1 is an axial cross section of a borescope viewing head and a detachable right angle prism assembly according to a first embodiment of this invention.

A first embodiment of this invention is ilusrated in FIGS. 1-5. With initial reference to FIGS. 1 and 2, a borescope 10 of six mm diameter is formed of a flexible insertion tube 11 having a viewing head 12 at the distal end thereof, the viewing head being a generally cylindrical protuberance of substantially five mm diameter. The head 12 has a flat front surface 13 and a cutout 14 at one position on its periphery. A forward-looking imager or viewing device 15 is situated in the front surface 13, alongside an elongated fiber optic illuminator 16. Projecting pins or studs 17, 18 extend radially from rear and front sides of the cylindrical viewing head 12. Here the pin 18 is positioned somewhat distally of the pin 17, so that the pins 17 and 18 define the unique attachment orientation.

Figure 3:
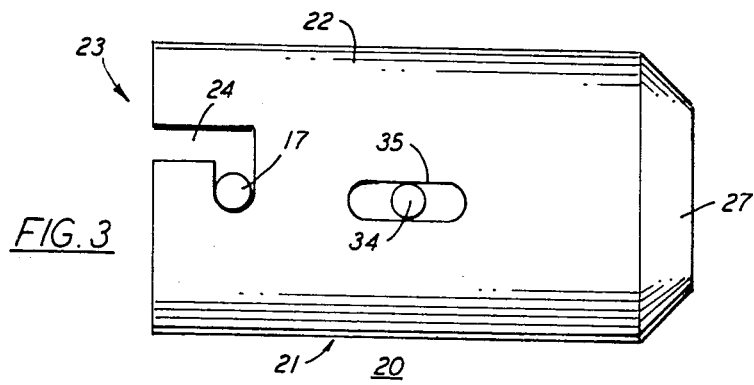
FIGS. 3 and 4 are rear and front views of the housing of the prism assembly according to the first embodiment of this invention, taken along lines 3—3 and 4—4 respectively of FIG. 1.
Figure 4:
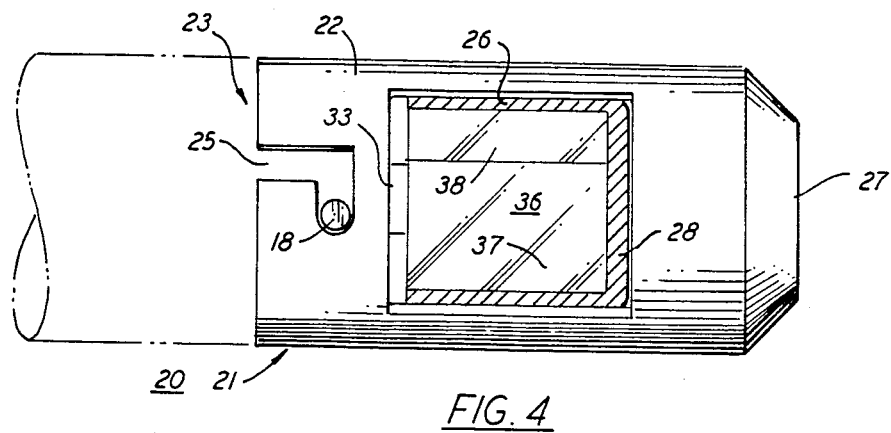
Figure 5:
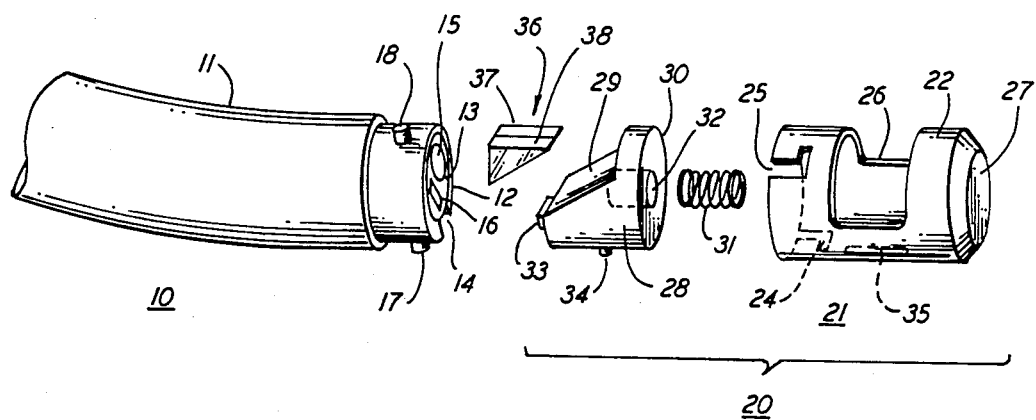
FIG. 5 is an exploded perspective assembly view of the borescope and detachable prism assembly of the first embodiment.

With reference also to FIGS. 3, 4 and 5 a detachable prism assembly 20 according to one embodiment of this invention converts the borescope 10 for right angle illumination and viewing. However, it is to be understood that somewhat retrograde, or other side-looking arrangements in addition to a right angle, would also be achieved employing the principles of this invention.

The assembly 20 has a housing, shown front and rear in FIGS. 3 and 4, the housing having a cylindrical side wall 22 with an open proximal end 23 to accommodate the viewing head 12, and L-shaped bayonet openings 24 and 25 which receive the retaining pins 17 and 18, respectively. As with the pins, the L-shaped openings 24 and 25 are of different heights, so that the prism assembly 20 can attach to the borescope 10 in only a single orientation.

The cylindrical housing 21 has a viewing opening 26 at the front thereof, as shown in FIGS. 1, 4, and 5. An end cap 27 closes off the distal end of the housing 21.

A prism holder 28, or slider is slidably fitted within the housing 21. The holder 28 has a slanted receiving surface 29 at its proximal side and a distal end face 30 which retains a compression spring 31 between a recess 32 in the distal end face 30 and the end cap 27 of the housing 21.

A tongue or detente 33 extends proximally and along the back side of the housing 21. This tongue 33 is urged by the spring 31 into engagement with the peripheral cutout 14 of the viewing head 12.

A finger pin 34 affixed on the back side of the sliding prism holder 28 extends out through an axial slot 35 in the back of the housing 21. This finger pin 34 is manually actuable to move the holder 28 to bring the tongue 33 forward and out of engagement with the cutout 14 so that the housing 21 can be twisted to release the pins 17 and 18 from the L-shaped openings 24 and 25 for removing the detachable prism assembly 20 from the borescope head 12. Finally, a right angle prism 36 is affixed onto the receiving surface 29 of the holder 28. As shown in FIGS. 4 and 5, the prism 36 is a split or two-part prism, comprised of a viewing prism 37 and an illuminating prism 38 cemented side by side so as to be disposed over the imager 15 and the illuminator 16, respectively.

To install, the prism assembly 20 is placed over the viewing head 12 and is rotated to locate the pins 17 and 18 in the openings 24 and 25. The housing 21 is then pushed proximally (to the left in FIG. 1) and then rotated again until the tongue 33 is aligned with the cutout 14. At that time, the spring 31 pushes the sliding holder 28 proximally to engage the tongue 33 in the cutout 14. This also urges the prism 36 against the front face 13 of the viewing head. Consequently, the prism 36 fits flush against the front face 13. However, because of the locking action of the tongue 33 and the cutout 14, the mating surfaces of the prism 36 and the viewing head 12 do not slide against one another, and therefore the likelihood of scratching either is minimized.

To release the detachable prism assembly 20 from the borescope 10, the tongue 33 must be disengaged from the cutout 14. This is accomplished by the user moving the pin 34 distally with his or her finger to move the prism holder 28 and tongue 33 forward. Then the housing can be rotated to disengage the L-shaped openings 24 and 25 from the retaining pins 17 and 18. The requirement for positive actuation of the pin 34 to uncouple the prism assembly makes it extremely unlikely that the prism assembly 20 would ever fall off the viewing end of the borescope 10 while an inspection of complex machinery or the like is underway.

Figures 2, 7:
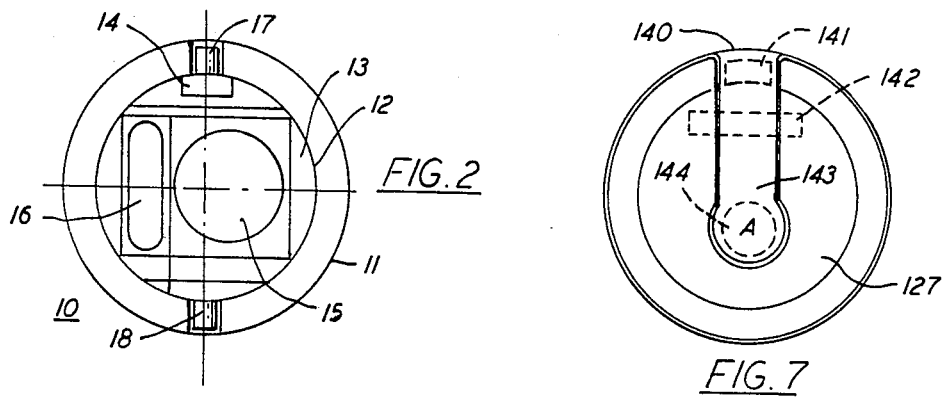
FIG. 2 is an end view of the distal end of the viewing head of the borescope.
FIG. 7 is an end plan view of the detachable prism assembly of FIG. 6, taken along lines 7—7.
Figure 6:
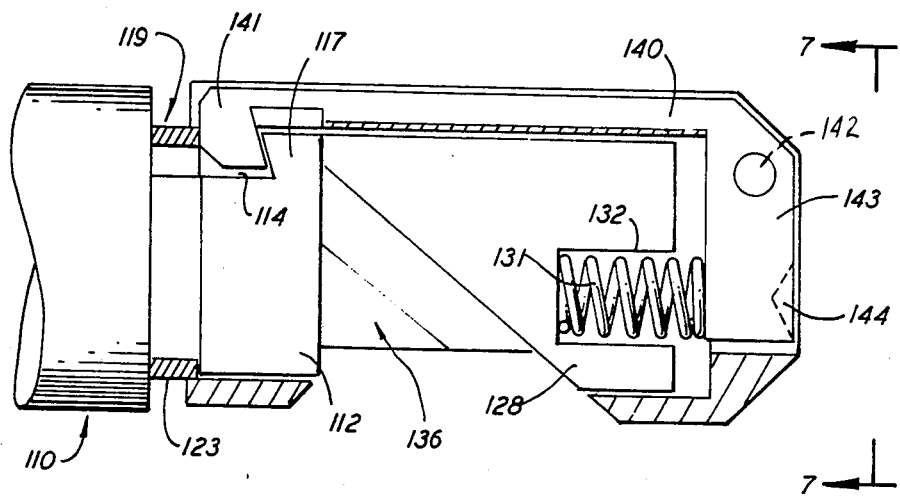
FIG. 6 is an axial cross section of a borescope head and detachable prism assembly according to a second embodiment of this invention.

A second embodiment of this invention is shown in FIGS. 6 and 7, and in the second embodiment elements that are similar to those of the first embodiment are identified with the same reference numbers, but raised by 100. In this embodiment, a borescope 110 has a viewing head 112 with a cutout 114 formed in one circumferential wall thereof, and a radially extending stop wall 117 is formed at the distal end of this cutout 114. A split ring 119 is located in an annular recess behind the viewing head 112. A detachable prism assembly 120 has a housing 121 formed of a generally cylindrical side wall 122 with an open proximal end 123, a front viewing opening 126 on a front side of the cylindrical wall 122, and a generally closed off distal end 127. A sliding prism holder 128 is similar to that of the first embodiment, but does not have an integral tongue corresponding to the tongue 33. A spring 131 is situated between a recess 132 in the holder 128 and the distal end 127 of the housing. A right angle prism 136 is mounted on the holder 128, and for all intents and purposes is identical with the prism 36 of the first embodiment.

In this prism assembly 120, an L-shaped retaining arm 140 extends on the housing 121 on the back side, that is on the side opposite the opening 126, and projects proximally back to the open end 123. An angled snap tab 141 at the proximal end of the arm 140 projects radially inward to fit into the cutout 114 in the head 112. Here, the tab 141 and the wall 117 are undercut or reversely angled so as to securely engage each other.

The retaining arm 140 is L-shaped and is pivotally mounted on a pivot pin 142 in the housing distal end 127. A distal face 143 of the retaining arm 140 disposed on the side of the pivot pin 142 opposite the tab 141 is urged outward, i.e., distally, by the coil spring 131. The tab 141 can move in and out of engagement with the cutout 114 by finger pressure at a location 144 on the face 143.

To install, the assembly 120 is rotated to locate itself on the head 112 and to orient itself so that the tab 141 snaps down into the cutout 114 and engages the angled or undercut wall 117. The retaining arm 140 will not snap down unless all of the required parts of the assembly 120 are in place and properly assembled, thus precluding partial attachment of the assembly 120 onto the borescope 110. The spring 131 loads the retaining arm 140 about the pivot pin 142 and also forces the prism 136 into contact with the front face of the head 112. Axial urging of the housing 121 away from the prism 136, holder 128, and head 112 loads the reversel angled surfaces of the tab 141 and the wall 117 for secure mutual engagement.

After the retaining arm 140 properly engages the head 112, a split ring 119 is rotated to trap the tab 141 so that the assembly 120 cannot simply pivot off the head 112.

To remove the detachable prism assembly 120 from the borescope 110, the split ring 119 is rotated to free the retaining arm 140, and the assembly housing 121 is pushed proximally, i.e., towards the head 112, while pressure is applied at the location 114.

Although the invention has been described in detail with reference to certain preferred embodiments, it should be understood that the invention is not limited to those precise embodiments, and that many modifications and variations would present themselves to those of skill in the art without departing from the scope and spirit of this invention, as defined in the appended claims.

What is claimed is:

1. A right angle detachable prism assembly for a small diameter borescope of the type that includes an insertion tube with a viewing head at its distal end, the head having a protruding member containing an optical image pickup device oriented along the axis of the head and through a flat front surface thereof, said protruding member having a peripheral cutout and radially projecting retaining means thereon; the prism assembly comprising

- a reflecting side-looking prism dimensioned to match said optical imager and having one flat face to be disposed against the flat front surface of the viewing head protruding member;
- a generally cylindrical housing disposed over said prism and having an open proximal end to fit over the viewing head protruding member with cooperating means therein which engage said retaining means;
- a prism holder slidably disposed in said housing including means securing said prism and oriented so that said one flat face is positioned against said protruding member front surface;
- a proximally extending projection which engages said cutout in said viewing head protruding member when said prism flat face is disposed against said front surface;
- means manually actuable from outside said housing to release said projection from said cutout; and
- resilient means for yieldably urging said prism holder proximally relative to said housing.

2. The right angle detachable prism assembly of claim 1, wherein said viewing head contains said image pickup device and an illumination device arranged side by side with separate respective windows in said front surface; and wherein said prism includes first and second individual prisms of like cross section taken perpendicular to the prism optic axis and affixed side by side on said holder.

3. The right angle detachable prism assembly of claim 1, wherein said prism holder has an angled proximal surface onto which the prism is mounted.

4. The right angle detachable prism assembly of claim 3, wherein said resilient means includes a compression spacing disposed between a distal end of said housing and a socket formed in a transverse distal surface of said prism holder.

5. The right angle detachable prism assembly of claim 1 wherein said means for releasing said projection from said cutout includes a radially projecting pin affixed on said prism holder and protruding through an axial slot on said housing.

6. The right angle detachable prism of claim 1 in which said proximally extending projection includes a tongue extending from the proximal end of said prism holder.

7. The right angle detachable prism assembly of claim 1, wherein said viewing head and said prism assembly housing have a bayonet fitting, said retaining means of said protruding member includes a pair of substantially oppositely disposed pins, and said cooperating means includes a pair of L-shaped slots opening onto the proximal end of said housing.

8. The right angle detachable prism assembly of claim 1, wherein said peripheral cutout on said protruding member and the proximally extending projection together define a unique assembly orientation of said prism assembly on said borescope viewing head.

9. The right angle detachable prism assembly of claim 1, wherein said cutout is disposed in a cylindrical wall of the viewing head protruding member, said radially projecting retaining means include an engaging wall at the distal end of the cutout, and said proximally projecting member includes an arm pivoted on said housing with a radially extending tab at its proximal end which reposes in said cutout and engages said engaging wall.

10. The right angle detachable prism assembly of claim 9, wherein said arm is in the form of an ell with a member disposed at the distal end of said housing and biased distally by said resilient means.

11. The right angle detachable prism assembly of claim 9, wherein said engaging wall and said tooth are reversely angled to ensure a positive engagement therebetween.

* * * * *